US006798526B2

(12) United States Patent
Brown et al.

(10) Patent No.: US 6,798,526 B2
(45) Date of Patent: Sep. 28, 2004

(54) METHODS AND APPARATUS FOR PREDICTING OXYGEN-INDUCED STACKING FAULT DENSITY IN WAFERS

(75) Inventors: Timothy L. Brown, Vancouver, WA (US); Dorothy E. Goff, Vancouver, WA (US); Romony K. San, Vancouver, WA (US)

(73) Assignee: SEH America, Inc., Vancouver, WA (US)

( * ) Notice: Subject to any disclaimer, the term of this patent is extended or adjusted under 35 U.S.C. 154(b) by 181 days.

(21) Appl. No.: 10/243,137

(22) Filed: Sep. 12, 2002

(65) Prior Publication Data

US 2004/0051882 A1 Mar. 18, 2004

(51) Int. Cl.[7] ................................................. G01B 11/30
(52) U.S. Cl. ..................... 356/600; 356/445; 356/237.5
(58) Field of Search ............................... 356/600, 394, 356/237.1–237.5, 445, 448; 117/13, 20, 932; 438/199, 401, 508–509; 257/E21.147, E21.321, E21.525, E23.179

(56) References Cited

U.S. PATENT DOCUMENTS

| 4,971,920 A | | 11/1990 | Miyashita et al. | |
|---|---|---|---|---|
| 4,981,549 A | | 1/1991 | Yamashita et al. | |
| 5,298,963 A | | 3/1994 | Moriya et al. | |
| 5,373,804 A | | 12/1994 | Tachimori et al. | |
| 5,478,408 A | * | 12/1995 | Mitani et al. ............... | 148/33.3 |
| 5,508,800 A | | 4/1996 | Miyashita et al. | |
| 5,625,451 A | | 4/1997 | Schiff et al. | |
| 5,677,208 A | | 10/1997 | Itou et al. | |
| 5,701,174 A | | 12/1997 | Yeh et al. | |
| 5,730,800 A | | 3/1998 | Sato et al. | |
| 5,903,342 A | | 5/1999 | Yatsugake et al. | |
| 5,933,229 A | | 8/1999 | Yeh et al. | |
| 6,097,428 A | | 8/2000 | Wu et al. | |
| 6,190,452 B1 | | 2/2001 | Sakurada et al. | |
| 6,266,137 B1 | | 7/2001 | Morinaga | |
| 6,275,293 B1 | | 8/2001 | Brown | |
| 6,292,259 B1 | | 9/2001 | Fossey et al. | |
| 6,292,260 B1 | | 9/2001 | Lin et al. | |

FOREIGN PATENT DOCUMENTS

| EP | 0702204 A2 | 3/1996 |
|---|---|---|
| EP | 0702204 B1 | 11/1999 |

* cited by examiner

Primary Examiner—Hoa Q. Pham
(74) Attorney, Agent, or Firm—Schwabe, Williamson & Wyatt, P.C.

(57) ABSTRACT

Methods and apparatus for predicting the density of oxygen-induced stacking faults (OSF) on a surface of a wafer by measuring the surface roughness before and after a surface damaging process is presented. Such damage can be produced by, but not limited to, a wet sand blast (WSB) process, a dry sand blast (DSB) process, lapping with an abrasive material, surface grinding, and by laser irradiation. The surface roughness resulting from the surface damage is quantified and compared with the pre-damaged surface roughness. The difference between the pre- and post-damaged surface roughness is determined and correlated with oxygen-induced stacking fault density to surface roughness correlation data to obtain the predicted oxygen-induced stacking fault density. An automated computer-assisted wafer OSF density evaluation apparatus is provided comprising a computer-based comparator comprising an electronic OSF correlation database and means for inputting pre- and post-damaged surface roughness data into the computer-based comparator, the comparator adapted to compute a delta surface roughness value, the delta being the difference between the post- and pre-damaged surface roughness data, the comparator adapted to correlate the delta surface roughness value with oxygen-induced stacking fault density to surface roughness correlation data to obtain the predicted oxygen-induced stacking fault density for the wafer.

22 Claims, 8 Drawing Sheets

| WSB Parameters | Units | WSB Process Tested | | | | | |
|---|---|---|---|---|---|---|---|
| | | 1 | 2 | 3 | 4 | 5 | 6 |
| Conveyer Speed | mm/min | 1000 | 1200 | 1200 | 1200 | 1200 | 1000 |
| Pump Pressure (speed) | Hz (cycles/sec) | 30 | 38 | 43 | 49 | 49 | 49 |
| Swing Arm Speed | RPM | 59 | 59 | 59 | 59 | 59 | 59 |
| Slurry Pressure (flowrate) | L/min | 5 | 5 | 5 | 5 | 5 | 5.6 |
| Air Pressure (nozzle) | kg-f/cm2 | 0.82 | 0.82 | 0.82 | 0.90 | 1.70 | 1.90 |

FIG. 6

| WSB CONDITION | 150mm P- Wafers | | | | | 200mm P+ Wafers | | | | |
|---|---|---|---|---|---|---|---|---|---|---|
| | ID | | PRE | POST | DELTA | ID | | PRE | POST | DELTA |
| 1 | Slot#2 | Average | 2.66 | 2.69 | 0.03 | Slot#3 | Average | 2.74 | 2.78 | 0.04 |
| | | Std Dev | 0.13 | 0.26 | | | Std Dev | 0.13 | 0.17 | |
| | Slot#3* | Average | 2.65 | 2.71 | 0.06 | Slot#4 | Average | 2.73 | 2.77 | 0.04 |
| | | Std Dev | 0.12 | 0.19 | | | Std Dev | 0.12 | 0.12 | |
| 2 | Slot#5 | Average | 2.66 | 2.74 | 0.08 | Slot#7 | Average | 2.79 | 2.84 | 0.05 |
| | | Std Dev | 0.12 | 0.27 | | | Std Dev | 0.14 | 0.15 | |
| | Slot#6 | Average | 2.66 | 2.75 | 0.09 | Slot#8 | Average | 2.78 | 2.84 | 0.06 |
| | | Std Dev | 0.12 | 0.16 | | | Std Dev | 0.13 | 0.12 | |
| 3 | Slot#8 | Average | 2.65 | 2.75 | 0.10 | Slot#12 | Average | 2.73 | 2.80 | 0.07 |
| | | Std Dev | 0.12 | 0.13 | | | Std Dev | 0.13 | 0.13 | |
| | Slot#9 | Average | 2.65 | 2.75 | 0.10 | Slot#11 | Average | 2.71 | 2.77 | 0.06 |
| | | Std Dev | 0.12 | 0.14 | | | Std Dev | 0.12 | 0.13 | |
| 4 | Slot#11 | Average | 2.65 | 3.80 | 1.15 | Slot#15 | Average | 2.76 | 3.51 | 0.75 |
| | | Std Dev | 0.12 | 0.18 | | | Std Dev | 0.13 | 0.23 | |
| | Slot#12 | Average | 2.65 | 3.79 | 1.14 | Slot#16 | Average | 2.74 | 3.50 | 0.76 |
| | | Std Dev | 0.12 | 0.18 | | | Std Dev | 0.13 | 0.18 | |
| 5 | Slot#14 | Average | 2.65 | 5.06 | 2.41 | Slot#18 | Average | 2.75 | 4.52 | 1.77 |
| | | Std Dev | 0.12 | 0.55 | | | Std Dev | 0.14 | 0.23 | |
| | Slot#15 | Average | 2.65 | 5.07 | 2.42 | Slot#19 | Average | 2.73 | 4.54 | 1.81 |
| | | Std Dev | 0.12 | 0.28 | | | Std Dev | 0.13 | 0.23 | |
| 6 | Slot#17 | Average | 2.62 | 6.38 | 3.76 | Slot#22 | Average | 2.74 | 5.57 | 2.83 |
| | | Std Dev | 0.13 | 0.31 | | | Std Dev | 0.2 | 0.41 | |
| | Slot#18 | Average | 2.68 | 6.45 | 3.77 | Slot#23 | Average | 2.73 | 5.60 | 2.87 |
| | | Std Dev | 0.12 | 0.39 | | | Std Dev | 0.13 | 0.31 | |

FIG. 7

| WSB CONDITION | 150mm P- Wafers | | | | | 200mm P+ Wafers | | | | |
|---|---|---|---|---|---|---|---|---|---|---|
| | ID | | PRE | ETCHED | DELTA | ID | | PRE | ETCHED | DELTA |
| 1 | Slot#2 | Average | 2.66 | 13.88 | 11.22 | Slot#3 | Average | 2.74 | 23.40 | 20.66 |
| | | Std Dev | 0.13 | 4.90 | | | Std Dev | 0.13 | 2.48 | |
| | Slot#3* | Average | 2.65 | 23.93 | 21.28 | Slot#4 | Average | 2.73 | 21.78 | 19.05 |
| | | Std Dev | 0.12 | | | | Std Dev | 0.12 | 0.89 | |
| 2 | Slot#5 | Average | 2.66 | 19.30 | 16.64 | Slot#7 | Average | 2.79 | 29.73 | 26.94 |
| | | Std Dev | 0.12 | 3.48 | | | Std Dev | 0.14 | 2.94 | |
| | Slot#6 | Average | 2.66 | 21.28 | 18.62 | Slot#8 | Average | 2.78 | 27.60 | 24.82 |
| | | Std Dev | 0.12 | 4.27 | | | Std Dev | 0.13 | 1.43 | |
| 3 | Slot#8 | Average | 2.65 | 20.95 | 18.30 | Slot#12 | Average | 2.73 | 30.44 | 27.71 |
| | | Std Dev | 0.12 | 3.47 | | | Std Dev | 0.13 | 2.59 | |
| | Slot#9 | Average | 2.65 | 22.67 | 20.02 | Slot#11 | Average | 2.71 | 31.04 | 28.33 |
| | | Std Dev | 0.12 | 5.63 | | | Std Dev | 0.12 | 2.74 | |
| 4 | Slot#11 | Average | 2.65 | 69.37 | 66.72 | Slot#15 | Average | 2.76 | 80.52 | 77.76 |
| | | Std Dev | 0.12 | 5.53 | | | Std Dev | 0.13 | 5.76 | |
| | Slot#12 | Average | 2.65 | 70.97 | 68.32 | Slot#16 | Average | 2.74 | 79.26 | 76.52 |
| | | Std Dev | 0.12 | 5.54 | | | Std Dev | 0.13 | 5.81 | |
| 5 | Slot#14 | Average | 2.65 | 102.13 | 99.48 | Slot#18 | Average | 2.75 | 104.93 | 102.18 |
| | | Std Dev | 0.12 | 6.80 | | | Std Dev | 0.14 | 4.44 | |
| | Slot#15 | Average | 2.65 | 103.42 | 100.77 | Slot#19 | Average | 2.73 | 104.44 | 101.71 |
| | | Std Dev | 0.12 | 6.85 | | | Std Dev | 0.13 | 4.51 | |
| 6 | Slot#17 | Average | 2.62 | 133.71 | 131.09 | Slot#22 | Average | 2.74 | 122.00 | 119.26 |
| | | Std Dev | 0.13 | 7.53 | | | Std Dev | 0.2 | 4.92 | |
| | Slot#18 | Average | 2.68 | 134.73 | 132.05 | Slot#23 | Average | 2.73 | 121.08 | 118.35 |
| | | Std Dev | 0.12 | 6.87 | | | Std Dev | 0.13 | 5.05 | |

FIG. 8

METHODS AND APPARATUS FOR PREDICTING OXYGEN-INDUCED STACKING FAULT DENSITY IN WAFERS

FIELD OF THE INVENTION

This invention pertains to determining oxygen-induced stacking fault density of wafers, and more particularly, to predicting extrinsic backside oxygen-induced stacking fault density by measuring surface roughness of a roughened wafer surface.

BACKGROUND OF INVENTION

Wafers used in the microelectronic industry, such as silicon (Si) and gallium arsenide (GaAs) wafers, are manufactured under stringent quality control with regards to contamination. During the manufacturing process, though, it is inevitable that contamination by elements will occur resulting in the wafer having undesirable electrical properties, possibly rendering a portion or the entire wafer useless. Transition metal contamination is of significant concern. The metal impurities can exist in a dissolved or precipitated state within the wafer, both of which produce deleterious effects. For example, dissolved transition metals can enhance carrier recombination which increases the background noise of a charge-coupled device (CCD) and increases the base current in bipolar devices. Additionally, metal impurities migrate to or precipitate at crystal interfaces which can degrade the dielectric strength of thin oxide layers, leading to gate oxide integrity (GOI) failures.

Removal of impurities from the active regions of the wafer by attracting the impurities to another region is generally referred to as gettering. One form of gettering is accomplished through a phenomena wherein crystal structural defects internal to the wafer act as precipitation sites for metal impurities. Some of these structural defects are oxygen precipitates and growth-related defects such as oxygen-induced stacking faults (OSF) and dislocation loops. During subsequent high temperature processes, the atoms of the metal impurities will migrate to the OSF locations and remain held there thus purifying the outer surfaces of the wafer. This type of gettering is generally referred to as intrinsic or internal gettering since it occurs with intrinsic OSF.

Another technique used to produce gettering properties that is particularly useful in preventing contamination from external sources as well as internal sources is to intentionally create extrinsic OSF. Extrinsic OSF relies on the phenomena whereby OSF will form in an oxidizing environment at crystal structure defects on a surface of the wafer. The active region of the wafer is referred to as the frontside; the region wherein electronic devices are produced. Extrinsic OSF is therefore typically produced on the backside of the wafer to draw the impurities away from the frontside.

One method of producing crystal defects which, in turn will produce OSF, is by producing backside damage (BSD) on the wafer. Wet sand blast (WSB) processes are known in the art to produce crystal defects in the form of surface roughening by blasting, at a predetermined pressure, a slurry of fine silicon dioxide powder and water directed against the backside surface of the wafer.

In subsequent oxidizing high temperature processes, OSF are formed at the defect locations. As a result, the impurities within the wafer migrate to the backside of the wafer and any external impurities, such as those found in high temperature furnaces, are attracted to the backside rather than depositing on the frontside of the wafer.

There is a balance between too little OSF to produce an effective gettering effect and too much OSF that renders the wafer with unacceptable electrical and structural properties. Therefore, in wafer production it is important to periodically monitor the effectiveness of the surface damaging process. A unit of measure used in the art is OSF density; that is, how many OSF's are present in a given surface area of the wafer. One crystal defect will generally correspond to one OSF.

One method of monitoring the effectiveness of the damage caused by the surface roughening process includes processing one or more monitor wafers along with the wafers of a production run of a particular shift. After the surface roughening process, the monitor wafer is removed from the production run and processed in a high temperature oxygen rich furnace to oxidize the damaged surface thereby creating OSF. Since the size of individual OSF is on the order of a few $Å_{rms}$ and difficult to measure using visual methods, additional surface modification is required. The damaged surface is exposed to a chemical etchant that selectively etches and enlarges the OSF sites forming enlarged OSF defects that can be detected visually under magnification.

A microscope is used for direct or photographic inspection of various locations of the damaged surface of the wafer. In one method, three standard locations on the damaged surface are inspected wherein the surface roughness is quantified by counting the visible defects in a predetermined area to determine defect density. A known linear relationship has been established that correlates OSF density wide defect density (U.S. Pat. No. 6,275,293, Brown, incorporated herein by reference). An average of the defect density at the standardized locations is used to determine the overall OSF density, which is extrapolated to the batch of wafers from which the monitor wafer was pulled.

The above process, though currently used in the industry, has a number of disadvantages. The process requires processing the monitor wafer in an oxidizing furnace, which is time consuming and contributes to testing variability. The wafer is etched in hazardous and toxic chemicals raising safety and environmental issues, and may lead to variability due to chemical concentration and temperature changes. The defects are manually counted which is a slow and tedious process that is prone to human error and lack of uniformity from one operator to the next. Only certain locations on the surface are inspected which provides limited information regarding the uniformity of the surface defects across the entire wafer. Also, the process is a destructive test wherein the monitor wafer is scrapped after evaluation.

It is common for this evaluation process to take two to three days to complete, by which time the production wafers have undergone extensive and expensive finishing steps and are awaiting release for shipment. If a quality issue arises, it is possible that all of the wafers produced in the particular shift will have to be scrapped at a significant cost to the producer. Also, if the production parameters have not been changed, wafers produced in subsequent shifts might be at risk of being scrapped, until the parameters can be adjusted.

Therefore, methods and apparatus are needed to determine OSF density of wafers that address these issues.

SUMMARY OF INVENTION

The present invention provides methods and apparatus for predicting the density of oxygen-induced stacking faults (OSF) on a surface of a wafer by measuring the surface roughness before and after a surface damaging process. In one embodiment of the method, surface damage is produced by a wet sand blast (WSB) process. The surface roughness resulting from the surface damaging process is quantified and compared with the pre-damaged surface roughness data. The difference between the pre- and post-damaged surface roughness data is determined and correlated with oxygen-induced stacking fault density to surface roughness correlation data to obtain the predicted oxygen-induced stacking fault density.

In another embodiment in accordance with the invention, automated computer-assisted wafer OSF density evaluation apparatus is provided that receives the wafer, measures the surface roughness over at least a portion of the surface, correlates the data with a predetermined database of OSF density data, and presents the predicted OSF density for that particular wafer.

The methods in accordance with the present invention replace, among other things, the wafer oxidizing and etching process. These methods address the variability in data resulting from manual inspection and counting, as well as furnace and chemical etchant fluctuations. The wafer quality evaluation can be obtained within hours rather than days, providing for a quick response to quality deviations prior to further finishing processes of the production wafers. Surface roughness variability is more completely and accurately determined since substantially the entire wafer surface can be evaluated. Further, since the OSF's have not been enlarged by an etching process, after the evaluation, the monitor wafer can be re-polished and reused, resulting in significant savings to the producer.

Further, the methods allow for an automated quality-monitoring process using surface-scanning machinery and computer-stored databases of surface roughness to OSF correlation data. Automation of the process is possible as a number of difficult to automate processes, including high-temperature oxidation followed by chemical etching, are eliminated. Further, the automated process removes the variability introduced by labor-intensive manual visual inspection under magnification and operator interpretation of the results.

These and other variations as well as the invention itself will become more readily apparent upon reference to the following detailed description that follows.

BRIEF DESCRIPTION OF DRAWINGS

FIG. 6 is a table defining six WSB process conditions, in accordance with an embodiment of the invention;

FIG. 7 is a table of pre- and post-WSB surface roughness data for the pairs of wafers that were not masked, in accordance with an embodiment of the invention;

FIG. 8 presents a table of pre-WSB and post etch surface roughness data for the pairs of wafers that were not masked, in accordance with an embodiment of the invention.

DESCRIPTION

In the following detailed description, reference is made to the accompanying drawings which form a part hereof wherein like numerals designate like parts throughout, and in which is shown by way of illustration specific embodiments in which the invention may be practiced. It is to be understood that other embodiments may be utilized and structural or logical changes may be made without departing from the scope of the present invention. Therefore, the following detailed description is not to be taken in a limiting sense, and the scope of the present invention is defined by the appended claims and their equivalents.

Although the following embodiments discuss the utilization of the wet sand blast (WSB) process for producing damage/crystal defects in the form of surface roughness, referred to as backside damage, other methods for producing surface damage can be used. The scope of the invention is not to be limited to the use of the wet sand blast process. The scope of the invention includes, but is not limited to, any process that would produce surface damaging on the wafer suitable for the intended purpose. Examples of other surface damaging methods that can be used to produce surface damage include, but are not limited to, abrasive erosion, including dry sand blasting (sometimes referred to as feather blasting), lapping with abrasive materials, surface grinding, and laser irradiation.

Although the following embodiments discuss silicon (Si) wafers as a wafer material, it is understood that the embodiments herein can also be applied to wafers comprised of other materials, such as gallium arsenide (GaAs), among others. Therefore, this disclosure is not limited to any particular wafer material known or yet to be known in the art.

Figure 1:
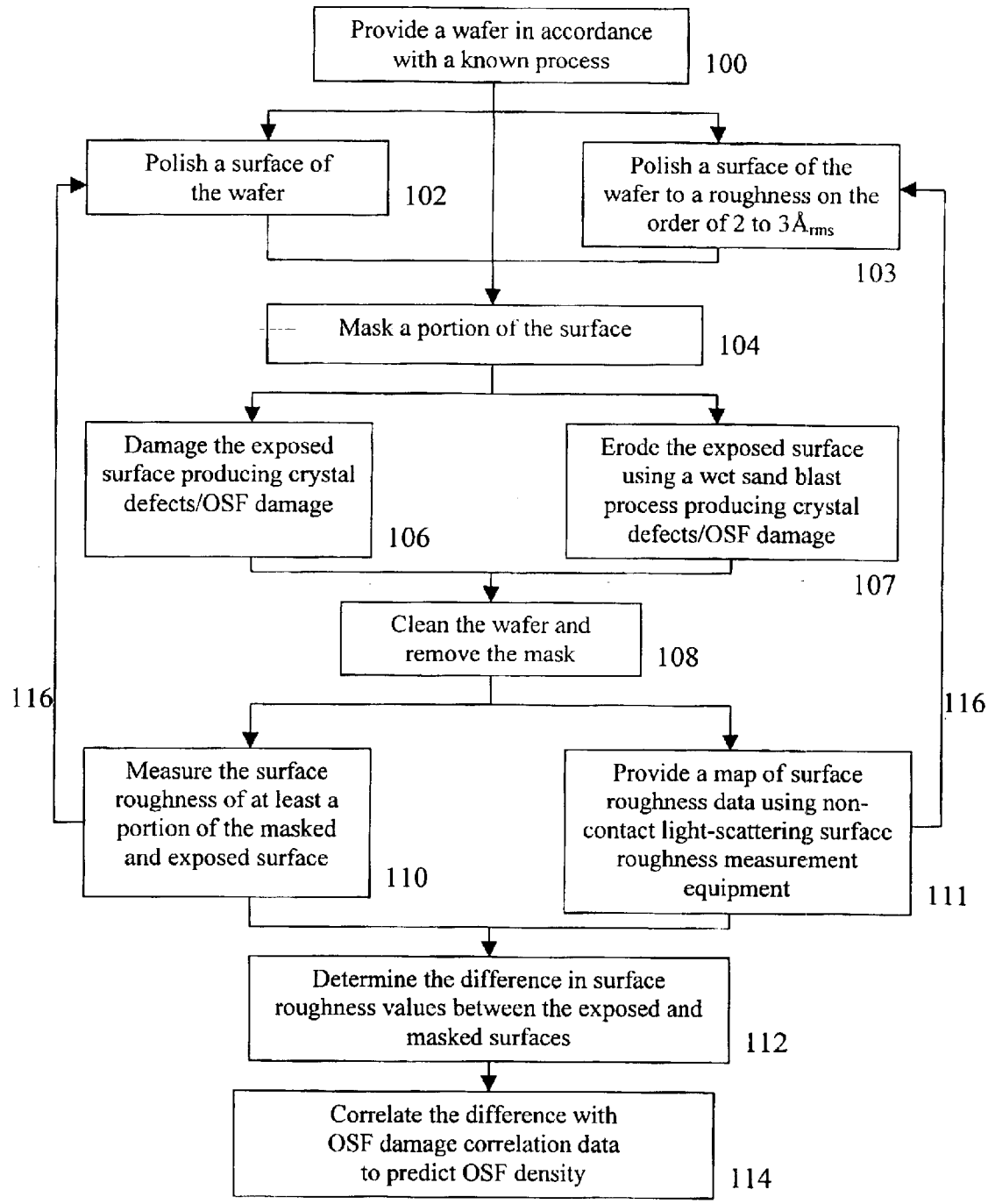
FIGS. 1 and 2 present flow diagrams of methods in accordance with embodiments of the invention.

FIG. 1 is a flow diagram of methods for predicting OSF density in accordance with embodiments of the invention. A wafer is provided using a process known in the art 100. A surface of the wafer is polished 102 to a surface finish appropriate to provide a measurable change in the surface roughness value between a pre- and post-surface damaging process. In one embodiment, the wafer surface is polished to a roughness on the order of approximately 2 to 3 $Å_{rms}$ 103. In another embodiment, no polishing is necessary as the as-received wafer has the appropriate surface polish 101. A protective mask is applied to a portion of the surface 104 which protects the covered portion from damage produced by subsequent processes. The exposed surface of the wafer is subjected to a process that produces surface damage on the wafer, and thus produces crystal defects 106. In one embodiment, the surface of the wafer is subjected to a wet sand blast (WSB) process that erodes the exposed surface 107. The wafer is cleaned to remove all traces of grit and to remove the mask 108 that has protected the portion of the polished surface. At least a portion of each of the protected and damaged surfaces is measured to determine surface roughness values using a surface roughness measuring device or by visual inspection 110. In one embodiment, the surface roughness of the wafer is mapped using non-contact light-scattering surface roughness measurement equipment 111. The difference between the surface roughness values of the damaged surface and the protected surface is determined providing a delta surface roughness (delta) value 112. The delta is correlated with established data that correlates between delta surface roughness and the OSF to establish a predicted OSF density for the wafer 114.

The mask material used to protect a portion of the surface can be any material that is suitable for the intended purpose.

Examples of suitable mask material include, but are not limited to, pressure sensitive adhesive tape, protective coatings such as photo-resist coating material, nitride and oxide layers.

There are a number of WSB processes known in the art that are suitable for producing surface damage. One example of a WSB process involves the placement of the wafer, backside up, onto a conveyor. The conveyor translates the wafer under one or more nozzles from which an abrasive slurry is expelled. The number of nozzles, their placement, whether the nozzles move in relation to the wafer, conveyor speed, slurry grit characteristics and delivery pressures are just a few of the parameters that can be adjusted to produce the desired surface roughness on the wafer. Wet sand blast equipment can be obtained commercially. One such manufacturer is Huan Shang Industrial Co., Taiwan.

Surface roughness measurements can be obtained using various contact and non-contact measuring equipment, as well as visual inspection. Due to the very small size and depth of the damage, the use of non-contact optical light-scattering surface roughness measuring equipment is especially advantageous. One supplier of such equipment is Schmitt Measurement Systems, Inc. (Portland, Oreg.). The Schmitt-TMS 3000 W is a non-contact microroughness measurement system using advanced light scatter technology suited for qualifying and quantifying full surface textures and zone microroughness. The Schmitt-TMS tool is well within its measurement capabilities to distinguish between a polished wafer surface roughness and the surface roughness created by the WSB process.

Figure 2:
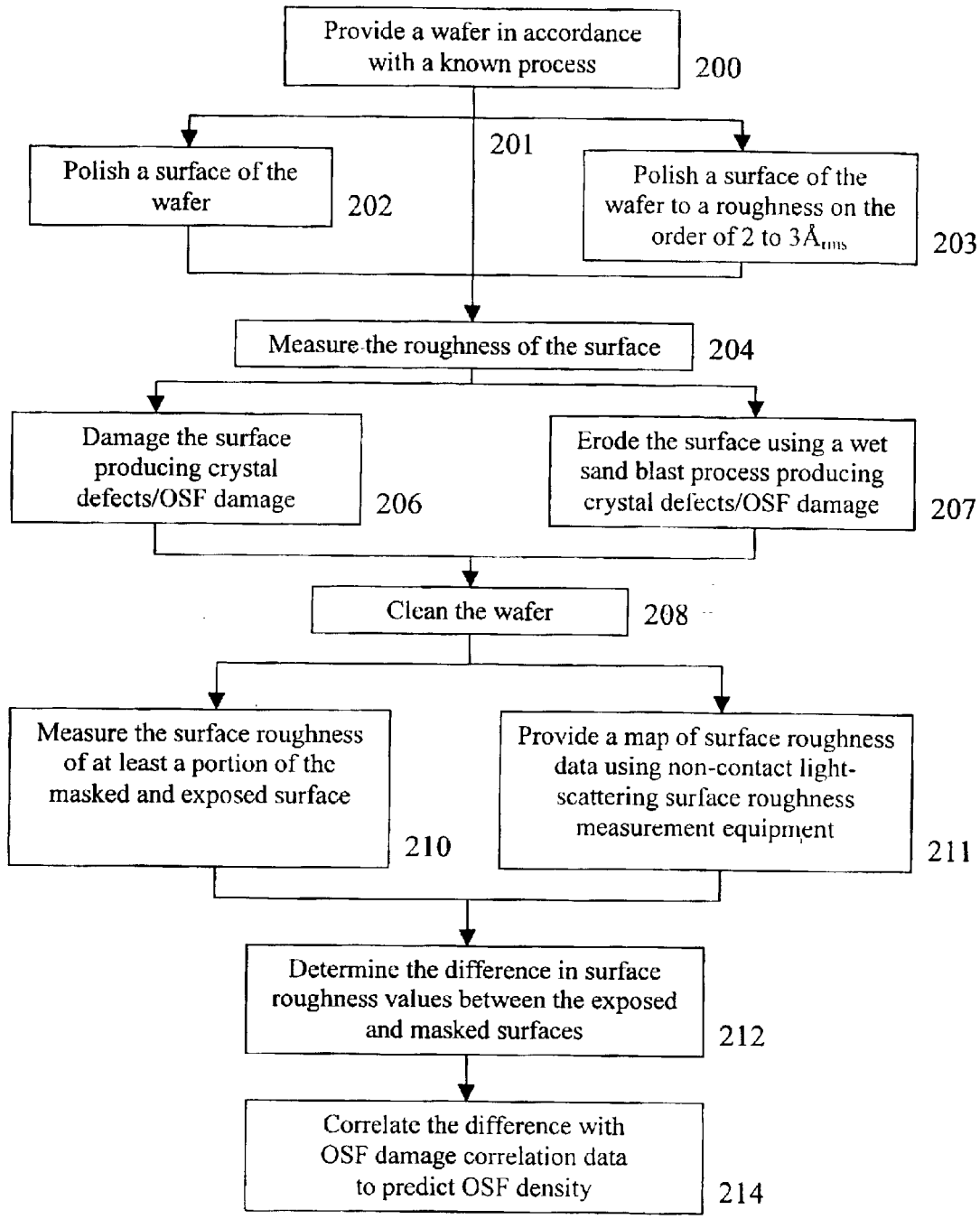

FIG. 2 is a flow diagram of other methods in accordance with embodiments of the invention. A wafer is provided using a process known in the art 200. A surface of the wafer is polished 202 to a surface finish appropriate to provide a measurable change in the surface roughness value between a pre- and post-surface roughness treatment. In another embodiment, the wafer surface is polished to a roughness on the order of approximately 2 to 3 $\text{Å}_{rms}$ 203. At least a portion of the surface of the wafer is measured for surface roughness using a surface roughness measuring device or by visual inspection 204. The surface of the wafer is subjected to a process that produces surface damage, and thus, produces crystal defects 206. In one embodiment, the surface of the wafer is subjected to a wet sand blast (WSB) process that erodes the surface 207. The wafer is cleaned to remove all traces of grit 208. At least a portion of the surface of the wafer is measured to determine the surface roughness value using a surface roughness measuring device or by visual inspection 210. In one embodiment, the surface roughness of the wafer is mapped using non-contact light-scattering surface roughness measurement equipment 211. The difference between the surface roughness values before and after the surface damaging process is determined providing a delta surface roughness (delta) value 212. The delta is correlated with established data that correlates between delta surface roughness and the OSF density to establish a predicted OSF density for the wafer 214.

In other embodiments in accordance with the invention, the wafer is polished to a level lower than 2 to 3 $\text{Å}_{rms}$. A surface roughness of approximately 1 to 2 $\text{Å}_{rms}$ would provide a larger delta between the pre- and post-surface damaging process. A larger delta would benefit the data interpretation of surface roughness measurements and uniformity and allow for more accurate OSF density prediction. However, the expense of more material being polished away, and the time and amount of slurry required to reach this improved polish, must be considered. It is understood that with a lower starting surface roughness value, the delta between the pre- and post-damage surface roughness will be a higher value, and therefore easier to measure. It is understood that it is not the absolute values of the pre- and post-damage surface roughness, but the relative values to determine the delta between the pre- and post-damage surface roughness values. It is also recognized that the processing time and expense will increase in order to produce a lower surface roughness surface. Therefore, a compromise between the resulting delta and the expense of producing a finer surface must be made. It has been found that a pre-damaged surface roughness of up to 10 $\text{Å}_{rms}$ produces satisfactory results, and depending on process perimeters and measurement equipment, higher pre-damaged surface roughness values are anticipated to be satisfactory.

Figure 3:
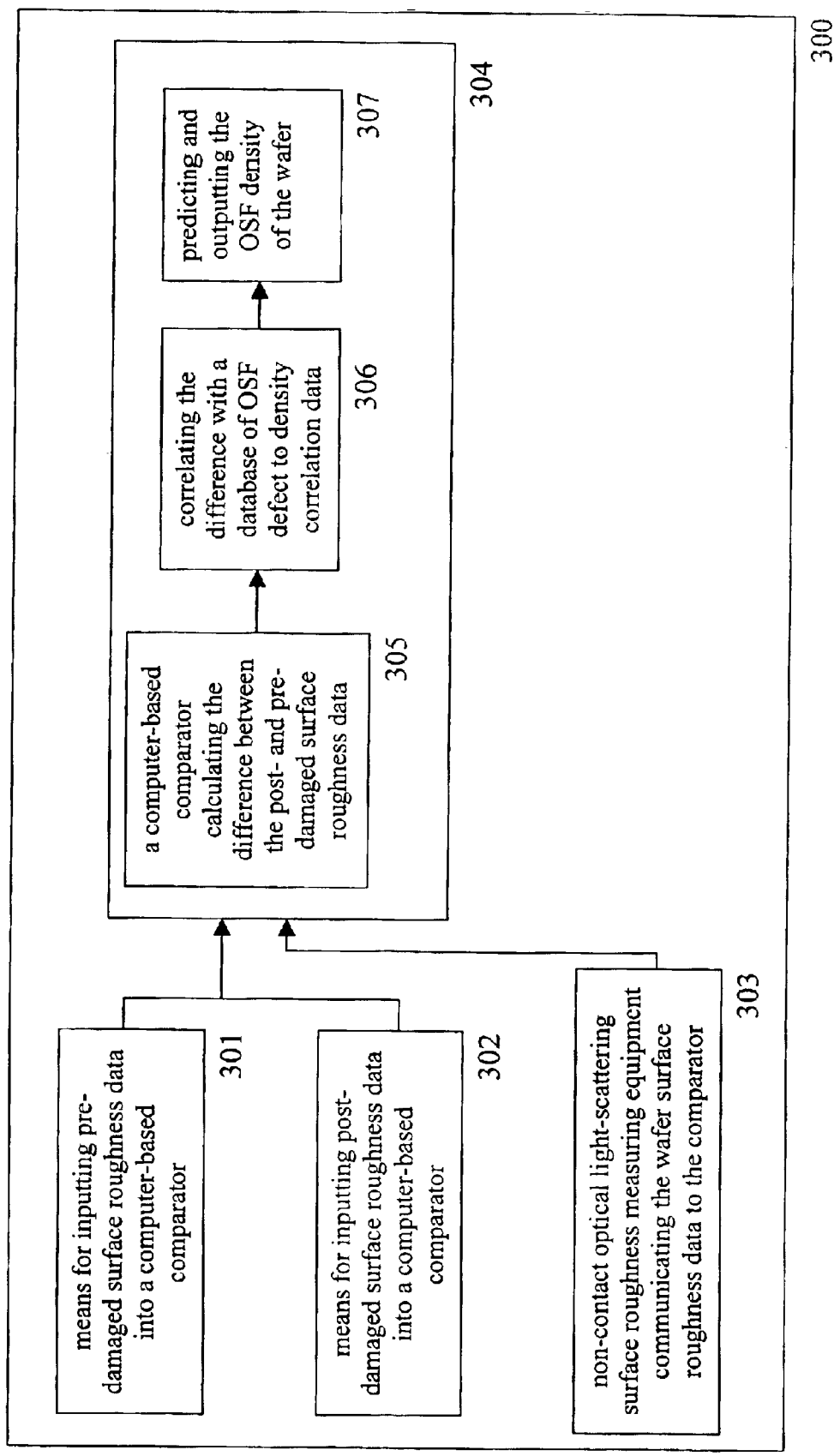
FIG. 3 is a flow diagram representation of an apparatus for the prediction of OSF in accordance with an embodiment of the invention.

FIG. 3 is a flow chart representation of an automated computer-assisted wafer OSF density evaluation apparatus 300, in accordance with an embodiment of the present invention. The evaluation apparatus 300 comprises means for inputting pre-surface roughened surface roughness data 301 and post-surface roughened surface roughness data 302 into a computer-based comparator 304. The comparator 304 compares the surface roughness data of the pre-damaged surface with that of the post-damaged surface and computes a delta surface roughness value 305. The delta surface roughness value is the difference between the post- and pre-damaged surface roughness data. The comparator correlates the delta surface roughness value with OSF correlation values stored in an electronic OSF correlation database 306. The results of the correlation is used to compute and output the predicted OSF density value for the wafer 307.

In one embodiment in accordance with the invention, non-contact optical light-scattering surface roughness measuring equipment 303 communicates the wafer surface roughness data to the comparator 304, providing the means for inputting surface roughness data into the computer-based comparator. The evaluation apparatus 300 accepts a wafer for processing. The surface of the wafer is illuminated such as with a laser while the wafer is translated and/or rotated about a predetermined path. The measuring equipment 303 determines whether the wafer is being processed in accordance with the methods presented in FIG. 1 or FIG. 2. Wafers processed in accordance with the methods of FIG. 1 will present a surface having both pre- and post-damaged surface roughness, since the mask protects a portion of the pre-damaged surface. The measuring equipment will provide surface roughness data from one or more portions of the pre- and post-damaged surface to the comparator 304. The measuring equipment 303 will determine which portion of the surface comprises the pre- and post-damaged conditions based on a predetermined threshold delta value between the pre- and post-damaged surface roughness values.

Wafers processed in accordance with the methods of FIG. 2 will be measured by the measuring equipment 303 twice. The first measurement will provide the as-polished, pre-damaged surface roughness data. After undergoing the damaging process, the wafer will be measured a second time to provide the post-damaged surface roughness data. The measuring equipment 303 will provide surface roughness data from one or more portions of the pre- and post-damaged surfaces to the comparator 304.

Figure 4:
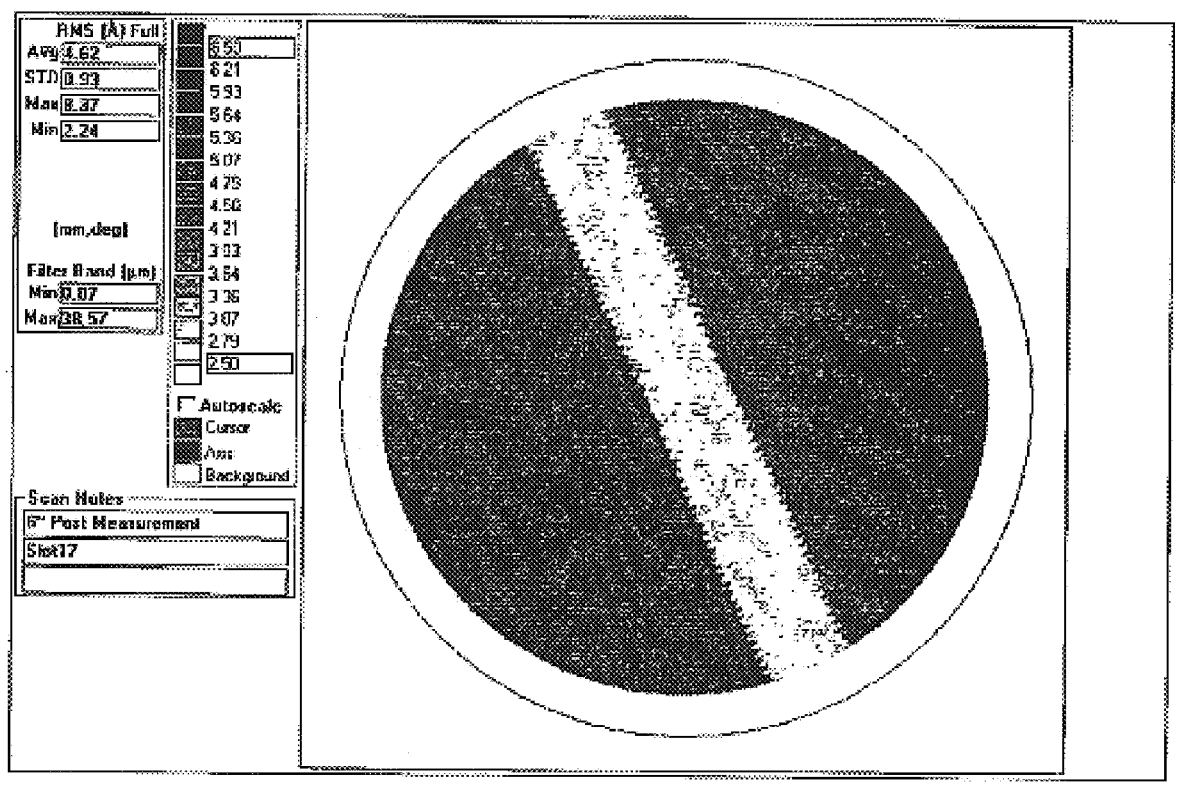
FIG. 4 is an example of a surface roughness mapping in accordance with the invention.

FIG. 4 is graphical representation in the form of a surface data map generated by non-contact optical light-scattering surface roughness measuring equipment measuring a wafer processed in accordance with the methods of FIG. 1. The effect of the mask in the form of a strip of tape can be seen traversing the image. Non-contact optical light-scattering surface roughness measuring equipment provides the benefit of measuring selected portions of the wafer surface or the entire wafer surface. A surface roughness map of the wafer surface can be produced showing the relative surface roughness of the wafer in graphical representation. Since the entire surface of the wafer is mapped, more precise measurements and averaging schemes can be used to produce more accurate predictive results.

Verification Tests

Figure 5:
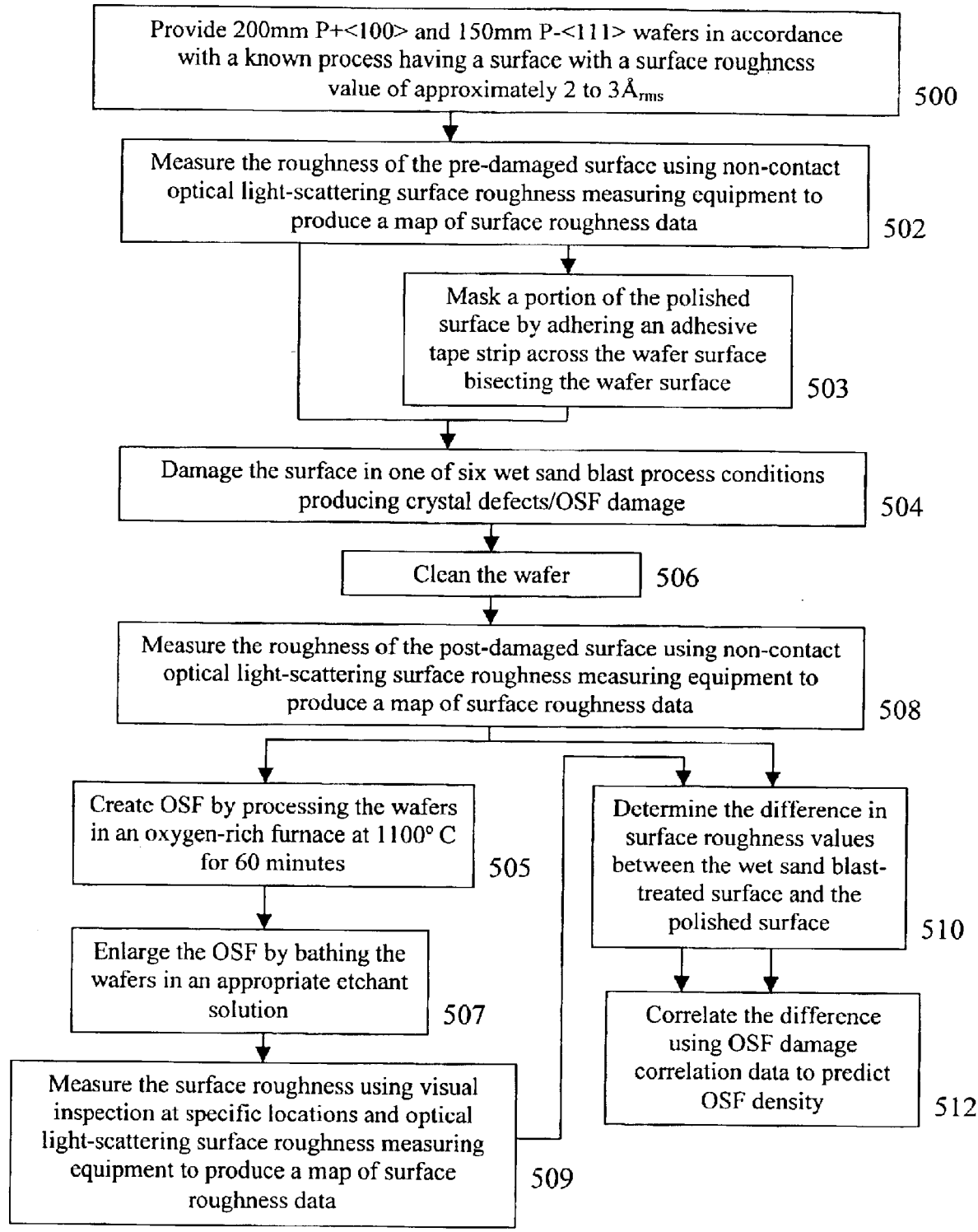
FIG. 5 is a flow diagram of verification processes in accordance with embodiments of the invention.

A series of verification tests were performed to establish the OSF density correlation data and to validate the effectiveness of the OSF density prediction process. FIG. 5 is a flow diagram of the verification process in accordance with an embodiment of the invention. A number of 200 mm P+ <100> (P+ wafer) and 150 mm P− <111> (P− wafer) silicon (Si) monitor wafers were prepared for evaluation. A monitor wafer is no different than a production wafer, only that the monitor wafer is used for quality evaluation. The backside surface of the wafers were polished to a surface roughness of approximately 2 to 3 $\text{Å}_{rms}$ 500. A map of surface roughness data for each wafer was established using the Schmitt-TMS non-contact microroughness measurement equipment 502. This measurement established the baseline surface roughness values to compare with the surface roughness values produced by a subsequent wet sand blast (WSB) damaging process.

FIG. 6 is a table defining the six WSB process conditions used in the testing. Six sets of three wafers of both wafer types were identified. One of the three wafers in each set had a portion of the surface masked using a strip of adhesive tape placed across the surface, bisecting the wafer 503. The mask prevented surface erosion of the surface under the masked portion during WSB processing. The mask was used to validate that it was possible to reliably determine pre- and post-damaged surface roughness with one surface roughness mapping. The six sets of both wafer types were processed using one of the six WSB conditions 504. The WSB process produces crystal defects/surface damage in the form of surface roughness.

After exposure to the WSB process, the wafers were cleaned to remove the mask, grit particles and other foreign matter 506. Post-WSB surface roughness values were mapped and recorded again using the Schmitt-TMS device 508. FIG. 7 is a table of pre- and post-WSB surface roughness data for the wafer pairs that were not masked.

In order to correlate the surface roughness value with OSF density values, both the masked and unmasked wafers underwent the standard process of oxidation and preferential etching. The wafers were subjected to a thermal cycle at 1100° C. for 60 minutes which caused the formation of OSF precipitated from the crystal defects to transform into an OSF 505. Following the thermal cycle, the wafers were preferentially etched to enlarge the OSF 507 forming OSF defects. Preferential etching involves the use of an etchant solution that attacks and dissolves the crystal structure of the OSF while leaving virgin wafer material intact. This etching enlarges the defects at OSF locations producing a larger difference between the pre- and post-damage surface roughness values, and produces surface features more readily identifiable during subsequent visual inspection. Data was measured using both optical microscope techniques and the Schmitt-TMS equipment 509. FIG. 8 presents a table of the pre-WSB treated and post-etching surface roughness data obtained using the Schmitt-TMS equipment. From this data, the delta, or surface roughness difference value, is obtained.

The surface roughness data obtained using visual inspection of each of the wafers was correlated with known and established correlation factors to obtain the OSF density. This OSF density data was used to correlate with and validate the OSF density predicted using the optically-measured surface roughness data.

Figure 9:
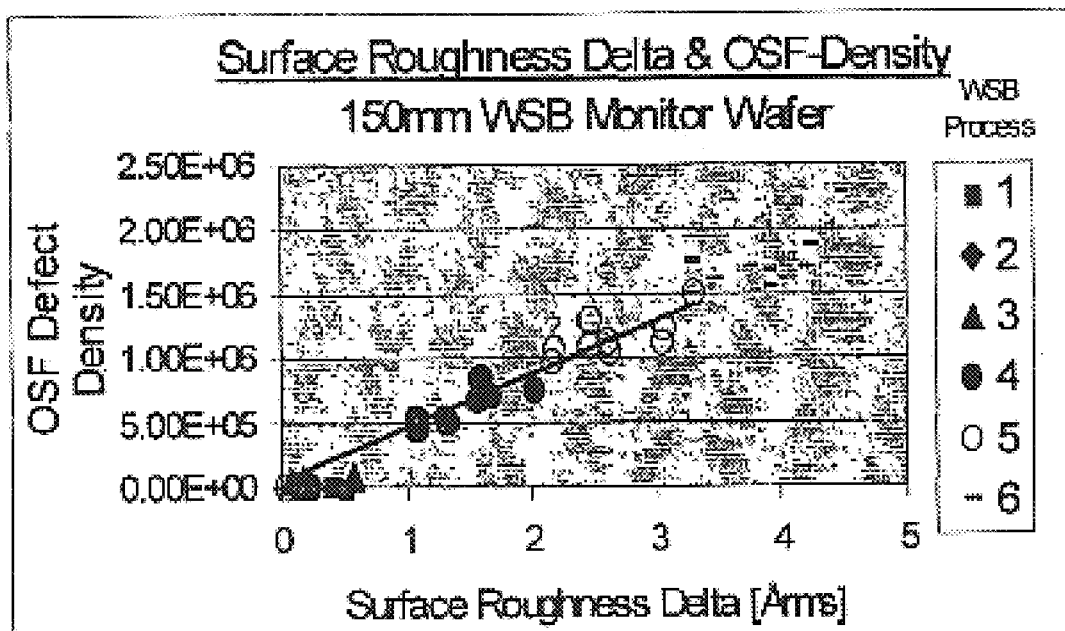
FIGS. 9 and 10 present graphs of the validation data obtained for the 150 mm P− <111> wafer and the 200 mm P+ <100> wafer, in accordance with an embodiment of the invention.
Figure 10:
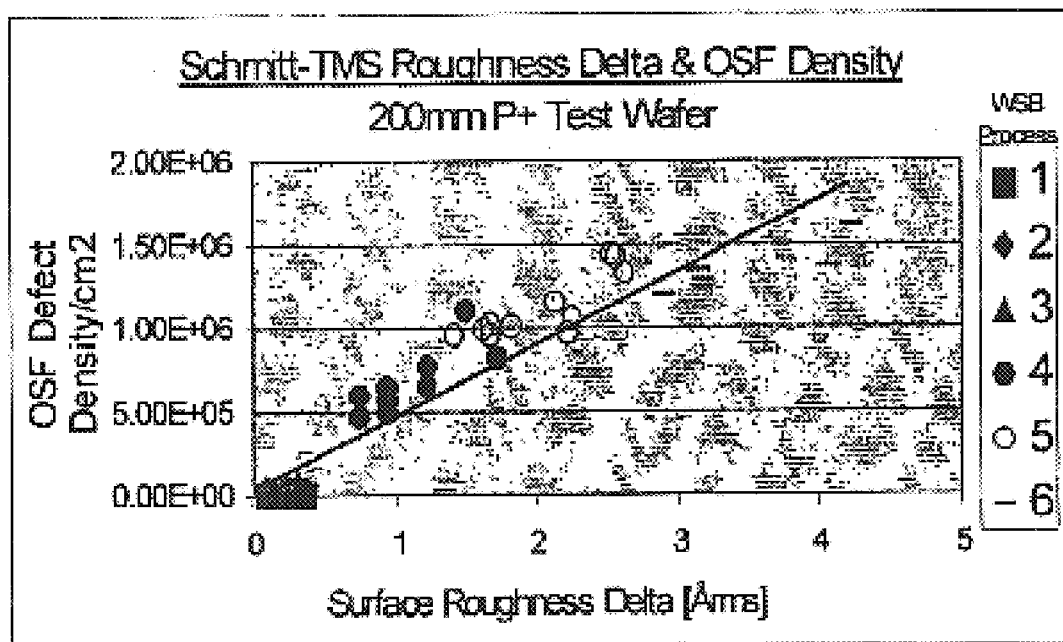

FIGS. 9 and 10 present graphs of the validation data obtained for the 150 mm P− <111> wafers (P− wafer) and the 200 mm P+ <100> wafers (P+ wafer), respectively, but for the wafer used in slot #3* under the 150 mm P− wafers which was a P− <100> wafer type. A surface roughness delta value (delta) is defined as the difference between the post-WSB surface roughness value and the pre-WSB surface roughness value. For the six WSB conditions, the delta was correlated with the OSF density determined using the standard visual inspection method. The graphs show a strong linear correlation ($r^2$ value) of 0.983 and 0.942 for the P− wafer and the P+ wafer, respectively, between the surface roughness delta and the OSF density. It is concluded that surface roughness measurement is a strong predictor of expected OSF density. By measuring pre- and post-WSB surface roughness values, the value of the OSF density can be determined from the linear relationship shown in FIGS. 9 and 10.

The surface roughness value mapping between the masked and not-masked P+ wafers were compared. No significant surface roughness value difference was seen between the exposed portions of the masked wafers and the surface of the not-masked wafers in any stage of the evaluation process: after the WSB process and after the etching. The polished surface roughness data for the two wafers is comparable at 2.71 $\text{Å}_{rms}$ for the masked wafer and 2.73 $\text{Å}_{rms}$ for the not-masked wafer. Similarly, the post WSB surface roughness data is comparable at 5.35 $\text{Å}_{rms}$ for the exposed surface of the masked wafer and 5.60 $\text{Å}_{rms}$ for the not-masked wafer, with the masked area retaining the pre-WSB surface roughness value. The post-etch surface roughness data for the wafers are comparable. It is concluded that the application of a mask on the wafer surface has no effect on the exposed surface roughness values before and after the surface damaging process, therefore, validating the masking method for obtaining pre- and post-damage surface roughness data simultaneously on one wafer.

A similar result was obtained for the P− wafers. The polished surface roughness data for the wafers is comparable at 2.65 $\text{Å}_{rms}$ for the masked wafer and 2.68 $\text{Å}_{rms}$ for the not-masked wafer. Similarly, the post-WSB surface roughness data is comparable at 5.69 $\text{Å}_{rms}$ for the exposed surface of the masked wafer and 6.45 $\text{Å}_{rms}$ for the not-masked wafer, with the masked area retaining the pre-WSB surface roughness value. The post-etch surface roughness data for the wafers are comparable. It is concluded that the application of the mask onto the wafer surface has no effect on the exposed surface roughness values before and after the surface damaging process, therefore, validating the masking method for obtaining pre- and post-damage surface roughness data simultaneously on one wafer.

Post-WSB surface roughness value mapping data, as well as surface roughness data and OSF density at four specific locations on the masked P− wafer, was recorded. Position 1 was protected from the WSB density by the mask and retained the as-polished surface roughness of 2.65 $\text{Å}_{rms}$. Positions 2, 3, and 4 were in separate areas of the surface that were not protected from the WSB damage. Position 2 had a surface roughness value of 5.95 $\text{Å}_{rms}$ correlating to an OSF density of 1.70E+06/cm$^2$, position 3 had a surface roughness value of 6.42 $\text{Å}_{rms}$ correlating to an OSF density of 1.76E+06/cm$^2$, and position 4 had a surface roughness value of 6.90 $\text{Å}_{rms}$ correlating to an OSF density of 1.87E+06/cm$^2$.

This data indicates that post-WSB surface roughness is fairly uniform across the surface that was exposed to the surface damaging process, that the mask did not influence or change the damage pattern produced by the WSB process, and that the surface of a monitor wafer can be partially masked to preserve the pre-WSB surface roughness and used as a reference for calculating the delta. This makes the OSF density determination process more efficient by not having to take two surface roughness measurements, the pre- and post-WSB measurements as required in the methods of FIG. 2, in order to determine the delta.

The surface roughness produced on the monitor wafer post-WSB damage is on the order of 5 to 7 $\text{Å}_{rms}$, unlike the 100 $\text{Å}_{rms}$ or more measured surface roughness value obtained with the oxidation and etching process currently used in the art. At this low level of damage, the wafer can be recycled by re-polishing to pre-WSB levels and used again 116, FIG. 1. This provides a great cost savings by not having to replace the monitor wafer after each evaluation.

The elapsed time to evaluate a monitor wafer in accordance with an embodiment of the invention is on the order of hours, not days, as for the standard process. The time necessary to polish the backside of the wafer is approximately 1 to 2 hours, if a polishing step is needed at all. It is anticipated that the provided wafers will have a suitably polished surface prior to the evaluation process and therefore, in that case, this initial polishing step is not needed. Applying the mask to a portion of the wafer surface can be as simple as the laying of pressure-sensitive adhesive tape or the application of a coating, by hand or by machine, in a matter of minutes. The WSB process requires 15 to 20 minutes, and the post-WSB cleaning process is approximately 1 to 2 hours. Actual measurement in the Schmitt-TMS equipment is under 5 minutes. The total time is well within that of a typical wafer production shift. It is understood that process efficiencies can be refined and improved to provide an even shorter processing time.

It is common in the art that silicon P− <111> wafers are used as monitor wafers, even for evaluating the production of P+ <100> wafers. The data presented in FIGS. 7–10 for the P+ <100> and the P− <111> wafers indicate that a P+ <100> wafer can be used as effectively as a P− <111> wafer as a monitor wafer with full satisfaction of the data needed to evaluate a production run of wafers. As such, a P+ <100> wafer from the P+ <100> production run can now be used as a monitor wafer for OSF density prediction. This provides a large cost savings and provides that data gathered from the monitor wafer will directly correlate and carry over with a high degree of confidence with the wafers in the production run.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiment shown and described without departing from the scope of the present invention. Therefore, it is manifestly intended that this invention be limited only by the claims and the equivalents thereof.

What is claimed is:

1. A method for predicting oxygen-induced stacking fault density on a surface of a wafer, comprising:
   providing a wafer;
   applying mask material on a portion of the surface, the mask material adapted to create a defect-free area by protecting the portion from exposure to a surface damaging treatment;
   exposing the surface to the surface damaging treatment producing defects in the form of surface roughness;
   removing the mask material, the surface characterized by a defect portion and defect-free portion;
   quantifying the surface roughness of at least one portion of the defect-free portion to obtain a first value;
   quantifying the surface roughness of at least one portion of the defect portion to obtain a second value;
   subtracting the first value from the second value to obtain a delta value; and
   correlating the delta value with oxygen-induced stacking fault density to surface roughness correlation data to obtain the predicted oxygen-induced stacking fault density.

2. The method of claim 1, the method further comprising:
   exposing the surface to a high-temperature oxidizing environment after obtaining the first and second values, the environment suitable for producing oxygen-induced stacking faults at the defects;
   exposing the surface to a chemical etching solution to preferentially etch the oxygen-induced stacking faults forming stacking fault defects;
   quantifying the stacking fault defects in at least one predetermined area of the defect portion to obtain a stacking fault defect density value;
   correlating the stacking fault defect density value with oxygen-induced stacking fault density to stacking fault defect density correlation data to obtain the predicted oxygen-induced stacking fault density; and
   correlating the predicted oxygen-induced stacking fault density based on the delta value of surface roughness with the predicted oxygen-induced stacking fault density based on the stacking fault defect density value.

3. The method of claim 1, wherein exposing the surface to a surface damaging treatment comprises exposing the surface to a process selected from the group consisting of abrasive erosion, wet sand blasting, dry sand blasting, lapping with abrasive materials, surface grinding, and laser irradiation.

4. The method of claim 1, wherein providing a wafer comprises providing a wafer selected from the group consisting of silicon (Si) and gallium arsenide (GaAs) wafers.

5. The method of claim 1, wherein correlating the delta value with oxygen-induced stacking fault density to surface roughness correlation data to obtain the predicted oxygen-induced stacking fault density comprises:
   inputting the wafer type and delta value into a computer-based comparator, the comparator comprising a database of oxygen-induced stacking fault density to surface roughness correlation data for predetermined wafer types, the comparator adapted to determine the predicted oxygen-induced stacking fault density by correlating the delta value with the oxygen-induced stacking fault density correlation data for the given wafer type.

6. The method of claim 1, wherein quantifying the surface roughness of the defect-free portion to obtain a first value comprises quantifying the surface roughness of the defect-free portion at more than one predetermined area within the defect-free portion and taking an average of the values to obtain a first value; and
   wherein quantifying the surface roughness of the defect portion to obtain a second value comprises quantifying the surface roughness of the defect portion at more than one predetermined area within the defect portion and taking an average of the values to obtain a second value.

7. The method of claim 1, wherein applying mask material to a portion of the surface comprises applying a piece of pressure sensitive adhesive tape to a portion of the surface, the pressure sensitive adhesive tape adapted to protect the portion from the surface damaging treatment.

8. The method of claim 1, wherein providing a mask material comprises providing a mask material selected from the group consisting of pressure sensitive adhesive tape and a coating material, including photo-resist coating material, nitride coating material, and oxide coating material.

9. The method of claim 1, wherein providing a wafer further comprises:
polishing the surface to an average surface roughness of no more than 10 $Å_{rms}$ prior to applying the mask material.

10. The method of claim 1, wherein providing a wafer further comprises:
polishing the surface to an average surface roughness to approximately 5 $Å_{rms}$ prior to applying the mask material.

11. The method of claim 1, wherein providing a wafer further comprises:
polishing the surface to an average surface roughness of between approximately 2 and 3 $Å_{rms}$ prior to applying the mask material.

12. The method of claim 1, wherein providing a wafer further comprises:
polishing the surface to an average surface roughness of no more than 2 $Å_{rms}$ prior to applying the mask material.

13. The method of claim 1, wherein quantifying the surface roughness comprises:
quantifying the surface roughness by utilizing non-contact optical light-scattering surface roughness measuring equipment suitable for quantifying the surface roughness in predetermined areas as well as over the entire surface creating a surface roughness value map.

14. A method for predicting oxygen-induced stacking fault density on a surface of a wafer, comprising:
providing a wafer;
quantifying the surface roughness of at least one portion of the surface to obtain a first value;
exposing the surface to the surface damaging treatment producing defects in the form of surface roughness;
quantifying the surface roughness of at least one portion of the post-damage surface to obtain a second value;
subtracting the first value from the second value to obtain a delta value; and
correlating the delta value with oxygen-induced stacking fault density to surface roughness correlation data to obtain the predicted oxygen-induced stacking fault density.

15. The method of claim 14, the method further comprising:
exposing the surface to a high-temperature oxidizing environment after obtaining the second value, the environment suitable for producing oxygen-induced stacking faults at the defects;
exposing the surface to a chemical etching solution to preferentially etch the oxygen-induced stacking faults forming stacking fault defects;
quantifying the stacking fault defects in at least one predetermined area of the post-etched surface to obtain a stacking fault defect density value;
correlating the stacking fault defect density value with oxygen-induced stacking fault density to stacking fault defect density correlation data to obtain the predicted oxygen-induced stacking fault density; and
correlating the predicted oxygen-induced stacking fault density based on the delta value of surface roughness with the predicted oxygen-induced stacking fault density based on the stacking fault defect density value.

16. The method of claim 14, wherein exposing the surface to a surface damaging treatment comprises exposing the surface to a process selected from the group consisting of abrasive erosion, wet sand blasting, dry sand blasting, lapping with abrasive materials, surface grinding, and laser irradiation.

17. The method of claim 14, wherein providing a wafer comprises providing a wafer selected from the group consisting of silicon (Si) and gallium arsenide (GaAs) wafers.

18. The method of claim 14, wherein correlating the delta value with oxygen-induced stacking fault density to surface roughness correlation data to obtain the predicted oxygen-induced stacking fault density comprises:
inputting the wafer type and delta value into a computer-based comparator, the comparator comprising a database of oxygen-induced stacking fault density to surface roughness correlation data for predetermined wafer types, the comparator adapted to determine the predicted oxygen-induced stacking fault density by correlating the delta value with the oxygen-induced stacking fault density correlation data for the given wafer type.

19. The method of claim 14, wherein providing a wafer further comprises:
polishing the surface to an average surface roughness of no more than 10 $Å_{rms}$ prior to the surface roughening treatment.

20. The method of claim 14, wherein quantifying the surface roughness comprises:
quantifying the surface roughness by utilizing non-contact optical light-scattering surface roughness measuring equipment suitable for quantifying the surface roughness in predetermined areas as well as over the entire surface creating a surface roughness value map.

21. An automated computer-assisted wafer oxygen-induced stacking fault density evaluation apparatus comprising:
a computer-based comparator comprising an electronic oxygen-induced stacking fault correlation database; and
means for inputting pre-damaged surface roughness data and post-damaged surface roughness data into a computer-based comparator, the comparator adapted to compare the pre-damaged surface roughness data with that of the post-damaged surface roughness data and compute a delta surface roughness value, the delta surface roughness value being the difference between the post- and pre-damaged surface roughness data, the comparator adapted to correlate the delta surface roughness value with oxygen-induced stacking fault correlation values stored in the electronic oxygen-induced stacking fault correlation database to compute and output a predicted oxygen-induced stacking fault density value for the wafer.

22. The apparatus of claim 21, wherein means for inputting pre-damaged surface roughness data and post-damaged surface roughness data into a computer-based comparator comprises non-contact optical light-scattering surface roughness measuring equipment suitable for quantifying the surface roughness in predetermined areas as well as over the entire surface creating a surface roughness value map, the measuring equipment in electrical communication with the comparator.

* * * * *

UNITED STATES PATENT AND TRADEMARK OFFICE
CERTIFICATE OF CORRECTION

PATENT NO. : 6,798,526 B2
DATED : September 28, 2004
INVENTOR(S) : Brown et al.

It is certified that error appears in the above-identified patent and that said Letters Patent is hereby corrected as shown below:

Drawings,
Figure 2, delete reference number "201".

Column 1,
Lines 62-63, "...OSF are..." should read -- ...OSFs are... --;

Column 2,
Line 7, "...OSF's are..." should read -- ...OSFs are... --;
Line 16, "...individual OSF is..." should read -- ...individual OSFs are... --;

Column 3,
Line 27, "...OSF's have..." should read -- ...OSFs have... --;
Line 61, "...post etch surface..." should read -- ...post-etch surface... --;

Column 4,
Line 44, "...polish 101." should read -- ...polish 102. --;

Column 7,
Line 66, "...value, is obtained." should read -- ...value, is obtained 510. --; and Column 8,
Line 2, "...surface roughness data." should read -- ...surface roughness data 512. --.

Signed and Sealed this

Seventh Day of February, 2006

JON W. DUDAS
*Director of the United States Patent and Trademark Office*